United States Patent
Heimes et al.

[11] 3,966,358
[45] June 29, 1976

[54] PUMP ASSEMBLY

[75] Inventors: Horst Peter Heimes, Aachen; Helmut Reul, Duren, both of Germany

[73] Assignee: Medac Gesellschaft fur Klinische Spezialpraparate mbH, Germany

[22] Filed: May 17, 1974

[21] Appl. No.: 471,057

[30] Foreign Application Priority Data
Nov. 9, 1973 Germany............................ 2355966

[52] U.S. Cl. .................................... 417/12; 417/18; 417/44; 417/45; 417/46; 3/1.7; 128/1 D
[51] Int. Cl.$^2$ ......................................... F04B 49/06
[58] Field of Search ............... 417/7, 18, 44, 46, 12, 417/45; 128/1 D; 3/1.7

[56] References Cited
UNITED STATES PATENTS

| | | | |
|---|---|---|---|
| 3,160,101 | 12/1964 | Bartoseski .............................. | 417/7 |
| 3,421,497 | 1/1969 | Chesnut ............................... | 128/1 D |
| 3,426,743 | 2/1969 | Chesnut ............................... | 128/1 D |
| 3,750,644 | 8/1973 | Ragsdale ............................. | 128/1 D |
| 3,842,440 | 10/1974 | Karlson ................................... | 3/1.7 |
| 3,882,861 | 5/1975 | Kettering .............................. | 417/44 |

*Primary Examiner*—William L. Freeh
*Assistant Examiner*—G. P. LaPointe
*Attorney, Agent, or Firm*—Cushman, Darby & Cushman

[57] ABSTRACT

A pump assembly is disclosed which includes a pump which is externally controlled to vary with time the volume and/or the pressure of fluid pumped therethrough. A memory unit is programmed to provide a desired volume-time and/or pressure-time characteristic. The output of the memory is utilized to drive the pump to provide the aforementioned pump characteristics. Provision is made for appropriately modifying the stored program in accordance with preselected parameters so that the pump can, for example, operate in conjunction with an artificial heart.

18 Claims, 6 Drawing Figures

PUMP ASSEMBLY

BACKGROUND OF THE INVENTION

This invention relates to a pump assembly including a pump which is externally controllable so that the volume and/or pressure of the fluid to be transported by the pump can be varied with time in a desired manner. More specifically, this invention relates to an externally controllable pump for pumping blood.

Pumps which are externally controllable to vary with time the volume and/or pressure of the fluid passing therethrough are known. For example, such pumps are utilized for supplying fuel to internal combustion motors. In these prior art pump assemblies, however, the control of the volume and/or pressure with respect to time customarily occurs only by mechanical means and, usually, control is possible only in response to the RPM of an internal combustion motor.

There are many instances, however, in which a particular supply or pressure curve is desired during the working cycle of the pump. For example, a blood pump should imitate the pumping "characteristics" of the natural heart as precisely as possible, especially if it is working in conjunction with an artificial heart. Moreover, such pump assemblies are desired for, among other things, artificial respiration devices, for dialyzers and for heart-lung machines. In addition, such pumps are also useful in different technological areas.

In order to achieve a desired timewise variance of the volume and/or pressure within each cycle of the pump, i.e., in order to achieve a particular pumping characteristic when using a pump assembly of the kind mentioned above, the pump is coupled to a programmable data memory unit which is programmed to correspond to the desired variation with time of the volume and/or pressure and which can be scanned at a controllable time-rate.

The desired pumping characteristic can be put into a programmable memory unit which, for example, can be a semi-conductor data storage or a number of sequentially addressable resistors whose values correspond to the program. In the latter case the resistors are sequentially addressable by a demultiplexer to which can be fed the time-sequential output signals of a binary counter, so that the pump conveys the fluid to be transported in accordance with the stored program during each operating cycle. For the purpose of controlling a blood pump, the pumping characteristics of the heart can be very precisely imitated in this way so that otherwise possible damage to the organism can be avoided.

The pump utilized in the present invention can be hydraulically driven and can be connected to a servo valve which supplies hydraulic fluid to the pump in accordance with the stored program. However, it is also possible to power the pump by a stepping motor which is itself controllable in accordance with the stored program or in the alternative, the pump may be a piston-type pump having a piston which is driven by a linear motor in accordance with a stored program.

In order to be able to read out the program in the memory unit in the desired time sequence and to utilize the program instructions for controlling the pump, a controllable clock generator is provided which is connected to the data storage through an address counter for the purpose of sequentially scanning of stored program. In order to achieve the desired time sequence, special control signals can be fed to the clock generator. The control signals can be derived, for example, from measured data. In a blood pump, the measured data can be obtained from the oxygen content of the blood and from the atrial pressure of the artificial heart so that the temporal sequencing for reading out the stored program can be appropriately established and, if necessary, modified.

If desired, the memory can also contain several programs for the volume-time and/or pressure-time characteristic of the pump simultaneously, and the pump system can be switched to the desired program by a program selector. In this case, the switch-over from one program to another in the memory can be made to depend on the output signal of the memory, for example, when the signal output passes through the value zero, so as to ensure continuity of blood circulation.

If a hydraulically driven pump having a servo-valve connected thereto is employed, a digital-to-analog converter can be connected between the data storage and the servo valve so that the output of the digital-to-analog converter provides the control signals for operating the servo valve. In addition, the output signal of the digital-to-analog converter can be fed to a maximum value decoder for generating a signal when the maximum amplitude of the output signal of the analog-to-digital converter occurs. That signal is used to control the clock generator for systolic or diastolic generation. Therefore, the clock generator generates two different clock-trains for addressing the memory. Such a signal is especially advantageous if the pump assembly is used, together with a blood pump, for supporting the natural blood circulation, for, in that case, the signal can serve to adapt the operation of the two pump mechanisms.

BRIEF DESCRIPTION OF THE DRAWINGS

The invention is more thoroughly explained hereinbelow with the aid of the figures which show schematic exemplary embodiments thereof.

DETAILED DESCRIPTION

Figure 1:
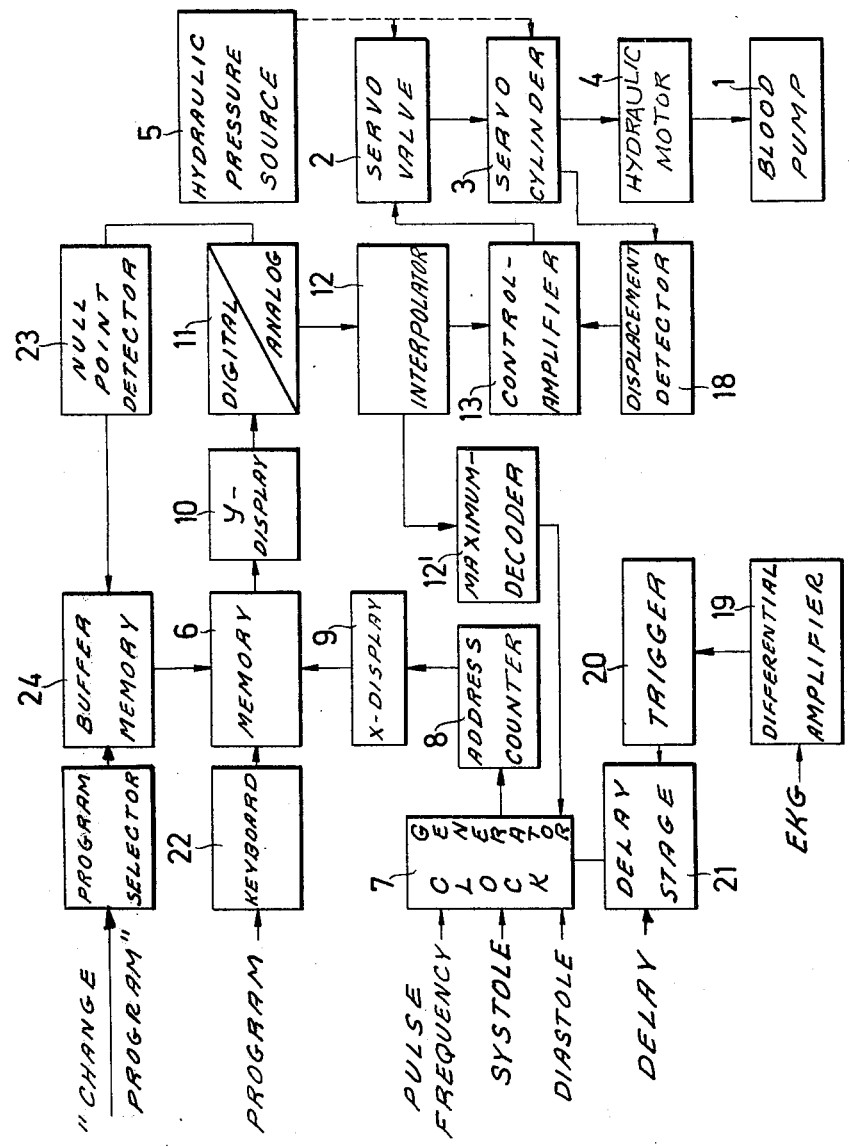
FIG. 1 is a block diagram of a pump assembly according to the invention including a blood pump with a servo valve.

An exemplary embodiment is illustrated in FIG. 1 which shows a pump assembly including a blood pump 1 which is driven by a servo valve 2 through a servo cylinder 3 and a hydraulic motor 4. The servo valve is of conventional design and the construction of the servo cylinder 3 and the fluid motor 4 will be explained hereinbelow with the aid of FIG. 2. The servo valve 2 and the servo cylinder 3 are each connected to a source of hydraulic fluid 5.

A programmable data storage or memory unit 6 serves as the essential element for controlling the blood pump and may be of any conventional design known in the art, such as, for example, a semi-conductor memory, a core storage or the like. The desired time variance of the volume of fluid pumped and/or the pressure generated by the pump is stored in this data storage element so that the pump can be correspondingly controlled by reading out the contents of the data storage 6. In order to read out the programmed data storage in a time-dependent or sequential manner, there is provided a time or clock generator 7 which generates readout pulses to the data storage in a time sequence determined by the clock generator. The output of the clock generator 7 is fed to an address counter 8 which in turn supplies an X-value 9 to the memory 6. The memory supplies the corresponding Y-value 10 which determines the displacement of the pump at a particular time to the digital-to-analog converter 11.

The output signal of the converter 11, which is a signal having a magnitude which varies non-uniformly or discontinuously, is fed to an interpolator 12 which produces a smoothly-varying output signal which serves to control the servo valve 2 via a P, PI or PID-type control amplifier 13. Each of the aforementioned elements including the smoothing circuit 12, the digital-to-analog converter 11 and the clock generator is of conventional design.

Figure 2:
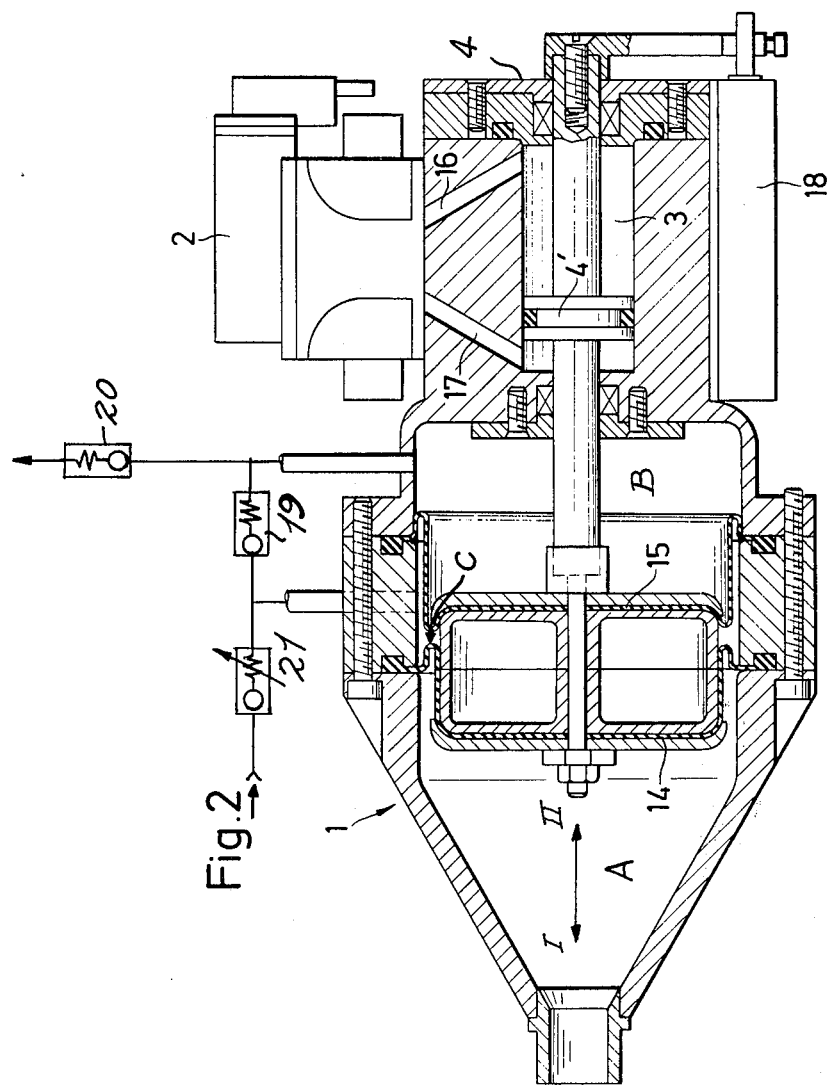
FIG. 2 is a schematic representation of the pump and of the servo valve connected to it.

When using the pump of the present invention, as shown schematically in FIG. 2, the sequence of operation is as follows. The servo valve 2, connected to the motor 4 supplies hydraulic fluid from the source 5 (FIG. 1) at a rate determined by the output of the control amplifier 13 via either the connecting channel 16 or 17, so that the pump piston 4' in FIG. 2 is displaced to the left or the right, respectively. If in the arrangement of FIG. 2, hydraulic fluid is supplied through the channel 17, then the piston 4' of the hydraulic motor 4 moves to the right. This causes the piston of the fluid motor 4 which is sealed by two opposing disc-shaped membranes 14 and 15 on its opposed surfaces and which is mechanically connected to piston 4' to move to the right. Thus, a suction stroke takes place. This motion of piston 4' to the right occurs in response to the program contained in the storage 6 (FIG. 1), i.e., the motion of the piston to the right varies with time as determined by the stored program and hence it can take place faster or slower in individual time segments in the pump cycle. This variation is achieved by a corresponding variation in the supply of hydraulic fluid to the pump cylinder 3. As a consequence thereof, the piston 4' of the blood pump also moves according to the program stored in the memory 6. It is clear that a corresponding movement of piston 4' to the left can be achieved by supplying hydraulic fluid, from servo valve 2, controlled by means of the program stored in the memory 6 through the channel 16.

Of particular importance is the manner in which the pressure is controlled in the membrane pump chamber C, to achieve a slightly negative pressure between membranes 14, 15, which is important for a correct function of membrane 14 in the suction mode. Referring to the figure, a valve 19 of conventional design is connected between a variable volume chamber B of the pump 1 and chamber C which is defined by the volume between the membranes 14 and 15. Another valve 20 is connected between the chamber B and a suitable outlet for the purpose of venting the chamber B when the piston moves in the direction II. A third valve 21 is connected to the chamber C in order to adjust the vacuum established in the chamber C.

In operation, if the piston is moving in direction I, a vacuum is generated in chamber B which is conveyed to chamber C through valve 19. Consequently, a vacuum is generated in the space between the two membranes 14 and 15 which avoids a collapsing of membrane 14 during the suction movement of the piston. The vacuum in chamber C is made adjustable by means of the adjustable valve 21. The vacuum is generated within a few strokes and is kept constant by the designed valve arrangement. During movement of the piston in direction II, the increase in pressure in the chamber B is vented through valve 20.

In general, it is necessary to check whether the movements of the piston 4' in the servo cylinder 3 take place according to the stored program to ensure that the actual movement of the piston is the same as the desired displacement. For this purpose, the servo cylinder 3 can be connected to a motion transducer 18 (FIGS. 1 and 2) which gives an output signal which corresponds to the actual displacement of the piston 4'. This output is fed to the control amplifier 13 so that, when the actual value of piston movement differs from the desired value thereof, a difference signal is generated to correct the movement of the piston to agree with the desired movement thereof.

As has already been mentioned, the pump assembly according to FIG. 1 can be used in conjunction with a blood pump. In that case, special operational conditions can occur which should be taken into consideration in the pump assembly. For example, the ratio of the systolic period to the diastolic period changes toward a shorter diastolic period with increasing pulse frequency. The program stored in memory 6 must therefore be adapted to change with the pulse frequency. For this purpose, signals corresponding to the pulse frequency as well as signals corresponding to the duration of the systole and diastole can be fed to the time generator 7 so that the timed scanning of memory 6 is changed by means of the time generator 7 according to the pulse frequency, i.e., when the pulse frequency increases, a shortened diastolic period is allowed for. Hence, it is unnecessary to alter the program in the memory 6, rather it is only necessary to change the time sequence of addressing memory 6 in accordance with the changed pulse frequency to thereby suitably modify the read-out of the stored program.

The pump assembly according to the invention can also be used to employ the blood pump in support of the natural blood circulation. For this purpose, the pump system can be supplied with an electrocardiogram which is fed via a differential amplifier 19, a trigger stage 20 and a delay stage 21 to the clock 7 to thereby control the time sequence of the read-out of the program stored in memory 6.

For model experiments or the like, it is often desirable to be able to switch back and forth among several programs for the operation of the pump, and it is also desirable that these different programs be stored in memory 6 before the experiments are started. To enable the switchover from one program to the next, there is provided a program selector switch which is connected to the buffer memory 24 to cause the transition from one program to another. In order to prevent the transition from one program to the next from leading to an abrupt or discontinuous change of conditions in the pump circulatory system, i.e., the circulation of blood, a null-value detector 23 is connected to the digital-to-analog converter 11. The detector 23 senses the passage of the output signal of memory 6 through the zero value, i.e., it determines the position of dead center in the operation of the pump and, at that position, causes via a buffer memory 24 the program change-over when the program switch 22 has been previously actuated.

The pump system of this invention preferably incorporates a maximum decoder 12' which produces a signal when the signal fed to the pump is at a maximum, the signal from the maximum decoder being used to control the clock generator. This is especially advantageous when the pump system is used in conjunction with a blood pump to assist the natural blood circulation, since then the maximum decoder signal can serve to control the operation of both pump mechanisms.

Figure 3:
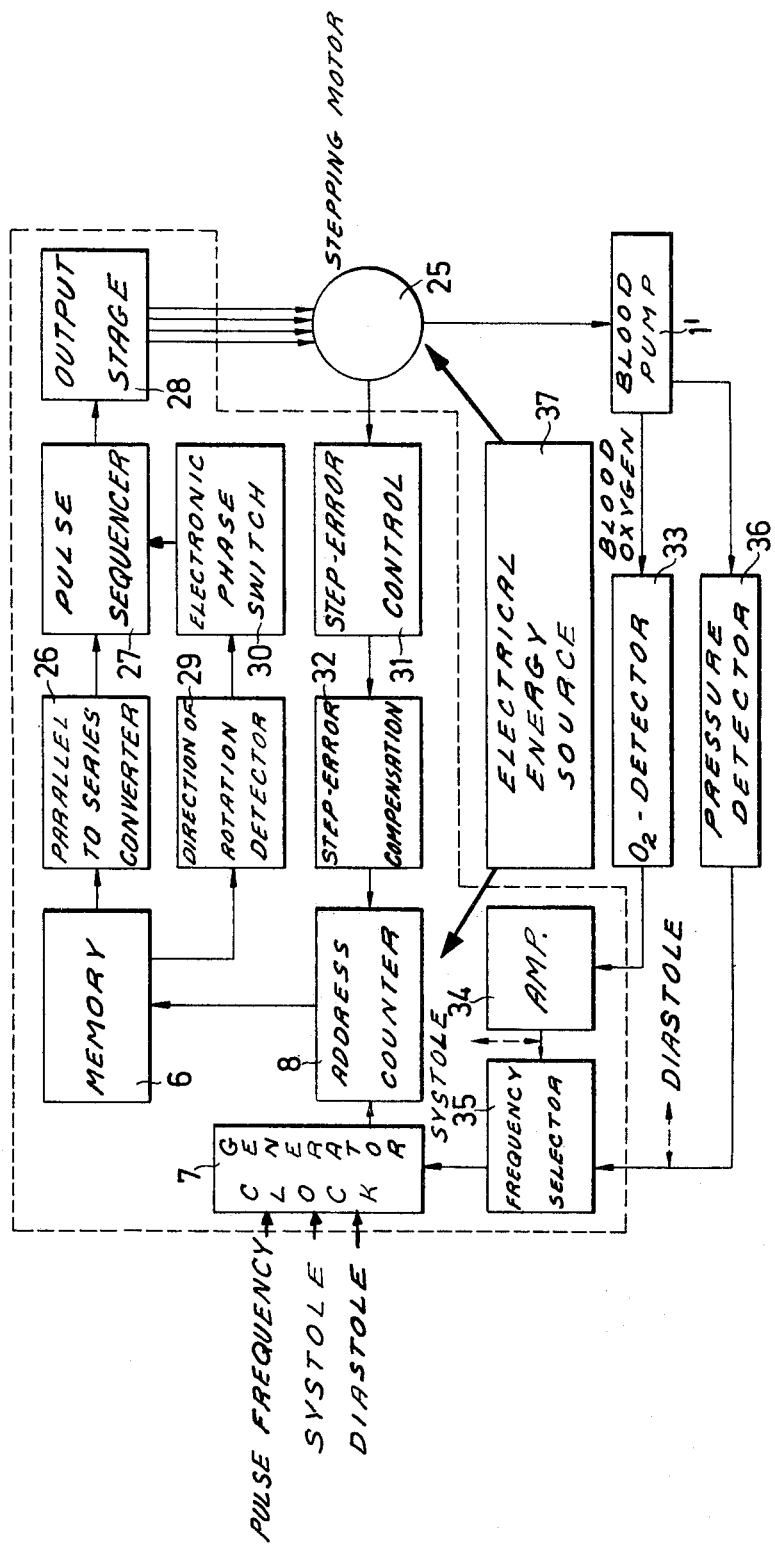
FIG. 3 is block diagram of another pump assembly according to the invention.

FIG. 3 is a block diagram of a somewhat modified exemplary embodiment of the invention, wherein a blood pump 1' is controlled in accordance with a program stored in memory 6. In this embodiment, the blood pump 1' is driven by a stepping motor 25 which moves in steps in accordance with the program and thus causes a corresponding volume-time and/or pressure-time operation of the pump. In order to control the operation of the stepping motor 25 in accordance with the stored programs, the binary-coded signals read out of memory 6 are fed to a parallel-to-series converter 26 whose serial output signals are supplied to a pulse converter 27, the output of which then drives the stepping motor 25 via an output stage 28.

In order to make certain that the stepping motor 25 rotates in the direction required by the program, a rotation direction sensor 29 is connected to the memory 6. The rotation direction sensor 29 operates via an electronic switch 30 to operate or control the pulse converter 27 and thereby guarantees the proper rotational direction of the stepping motor 25.

Deviations of the stepping motor from the required position are fed to the address counter 8 via the step-error control 31 and the step-error compensator 32, thereby effecting an appropriate correction of the scanning of storage 6 via the address counter 8.

When the blood pump 1' is used to operate an artificial heart, it is necessary to determine the durations of systole and diastole. In order to control the duration of the systole, an oxygen sensor 33 is used and it operates a frequency selector 35 via an amplifier 34. This frequency selector determines the pulse frequency in dependence on the output signal of the oxygen sensor 33. A pressure sensor 36 monitors the pressure in the auricle of the artificial heart and, by means of the frequency switch 35, it controls the clock generator 7, so that the auriclar pressure can never be negative.

The control portion of the pump assembly according to FIG. 3 can be constructed in the form of an integrated circuit as is indicated by the broken lines wherein the integrated circuit can be supplied by a suitable energy source 37 which also energizes the stepping motor 25.

Figure 4:
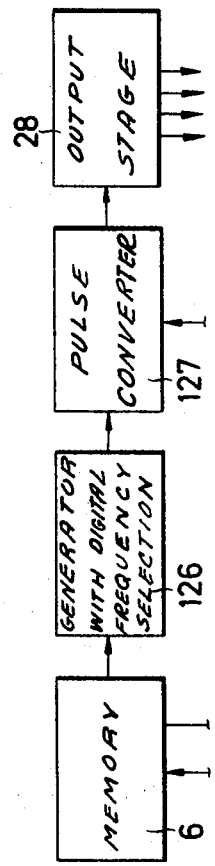
FIG. 4 is a schematic block diagram showing the elements connected to the data storage for the purpose of altering the pump assembly of FIG. 3.

As a modification of the pump assembly according to FIG. 3, a generator 126 having digital frequency selection can be connected to the memory 6, as illustrated in FIG. 4, in place of the parallel-to-series converter 26 illustrated in FIG. 3. This generator produces in accordance with the binary-coded output signals of memory 6 various frequencies which are fed to the pulse converter 127 whose output in turn drives the stepping motor 25.

Figure 5:
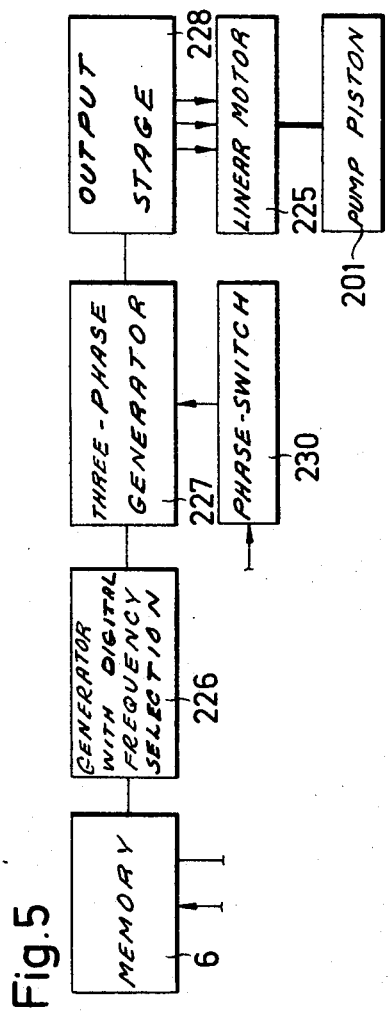
FIG. 5 is a block diagram showing the modifications in the pump assembly of FIG. 3 when using a piston-type pump driven by a linear motor.

As illustrated in FIG. 5, the pump system can be further modified to include a linear motor 225 acting directly upon the pump piston 201. In this arrangement, the output signals of the memory 6 are fed to a generator 226 with digital frequency selection. The varying output frequency from this generator controls a polyphase generator 227 which drives the linear motor 225 via the output stage 228. A phase selector 230 which is coupled to the memory 6 serves to control the direction of motion of the linear motor. The advantage of this modification is that no mechanical rotation-translation-transformation is needed.

Figure 6:
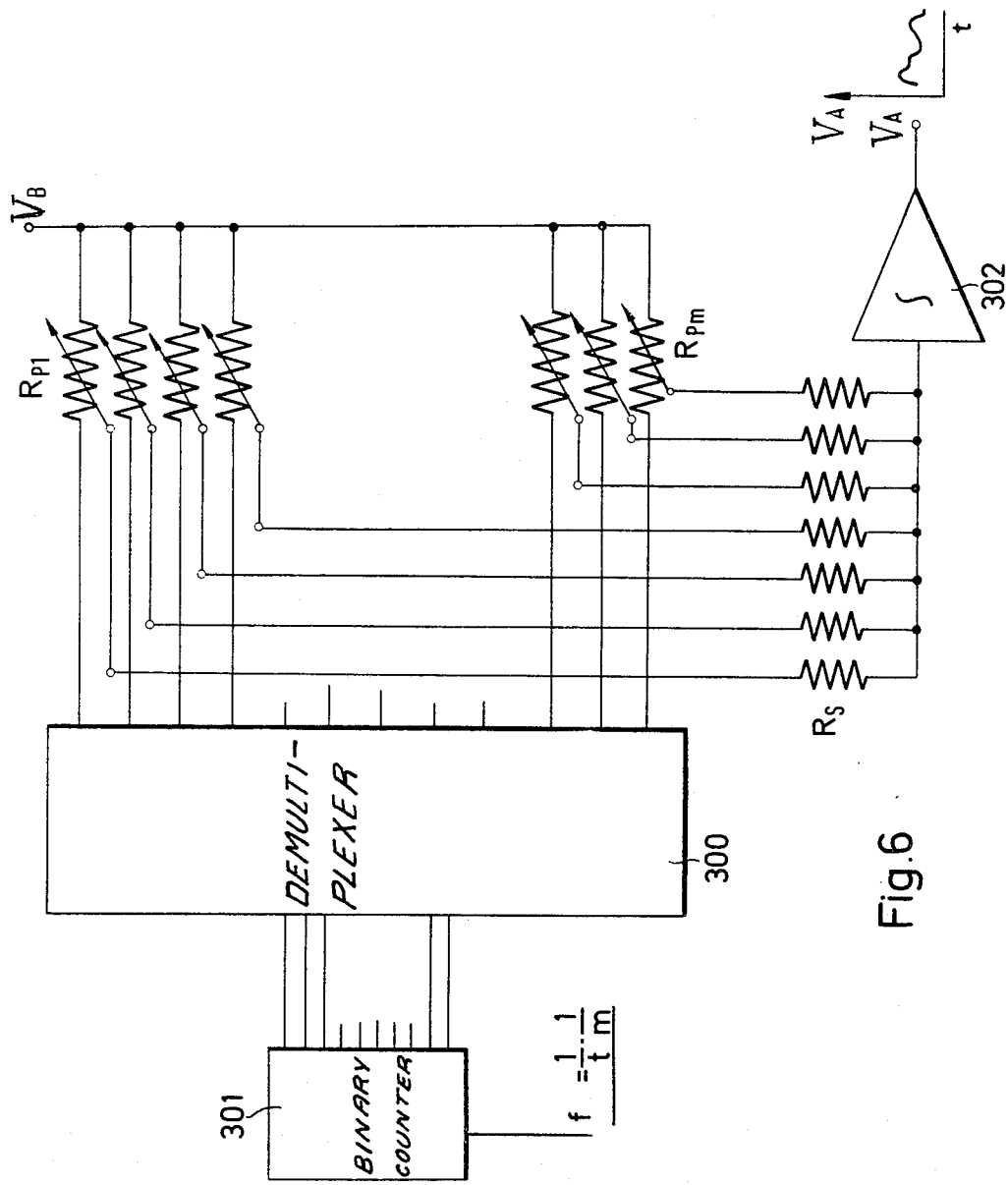
FIG. 6 schematically illustrates an exemplary embodiment of a programmable data storage usable in the pump assembly.

While it has been assumed above that the memory 6 is a digital storage unit which delivers primarily digital or binary-coded output signals, the storage can also be constructed so that its output signal is in analog form. An example of such an analog storage is illustrated schematically in FIG. 6. This storage takes the form of a function generator containing a number of resistors $R_{P1}$ to $R_{Pm}$, which are preferably variable resistances. One end of these resistors is connected to a voltage source $V_B$ and the other end is connected to the output of a demultiplexer 300 whose inputs are connected to the outputs of a binary counter 301. When this storage is utilized in a pump assembly for a blood pump, the binary counter 301 is driven with an input frequency $f_{in} = 1/t \cdot 1/m$ where t is the duration of the period of the heart pulse and m is the number of resistors $R_p$. During each pulse period, the counter 301 delivers m different counts to the demultiplexer 300. The demultiplexer 300 via its outputs applies a voltage successively to the resistors $R_{P1}$ to $R_{Pm}$. Through the summing resistors $R_S$, one each connected to a selected pickoff point of a corresponding resistor $R_P$, the voltage drop at the pickoff point of the resistors $R_P$ is fed to an integrator 302 whose output signal thus corresponds to the program set up by appropriately varying the resistors $R_P$. The memory according to FIG. 6 can be used, for example, to control the servo valve in the pump assembly illustrated in FIG. 1 without the use of a digital-to-analog converter.

What is claimed is:
1. A pump assembly comprising
a pump, said pump having a piston therein,
a programmable memory for storing a preselected amplitude, frequency and wave-shape variable fluid pumping characteristic,
means for reading out the fluid pumping program stored in said memory,
means for controlling the displacement of said piston in said pump to provide a fluid pumping characteristic in accordance with said stored program,
means for comparing the position of said pump piston with the position thereof established by said stored program, and
means responsive to said comparing means for controlling said pump piston to correct any deviation of the piston position from the position established by said stored program.

2. The pump assembly of claim 1 wherein said controlling means comprises a digital-to-analog converter, said converter having its input connected to the output of said memory and its output connected to said pump.

3. The pump assembly of claim 2 further comprising a maximum value decoder connected to the output of said digital-to-analog converter for producing a signal when the output of said converter is at a maximum amplitude.

4. The pump assembly according to claim 1 further comprising a stepping motor for driving said pump, said motor being controlled in accordance with said stored program.

5. The pump assembly of claim 1 further comprising a linear motor and wherein said pump is a piston-type pump, said piston being driven by said motor and said motor being controlled in accordance with said stored program.

6. The pump assembly of claim 1 further comprising a controllable clock generator, and an address counter connected to the output of and being driven by said clock generator, said address counter time sequentially scanning said memory to readout said stored program.

7. The pump assembly according to claim 1 wherein said memory is a semi-conductor storage.

8. The pump assembly according to claim 1 wherein said memory includes a plurality of sequentially addressable resistors, said resistors having values which correspond to the desired movement of said pump at each of a plurality of sequential time intervals, and demultiplexer means for sequentially addressing and reading out each of said resistors at predetermined time intervals.

9. The pump assembly of claim 1 further comprising means for storing a plurality of different programs in said memory, each of said programs having a preselected fluid pumping characteristic and means for selectively reading out one of said plurality of programs.

10. The pump assembly of claim 12 further comprising a null-value detector connected to the output of said memory, said detector permitting the program of said memory to be switched.

11. The pump assembly of claim 1 wherein said program controls the volume and pressure of said fluid pumped through said pump with respect to time.

12. The pump assembly of claim 11 wherein said pump further comprises a piston means for pumping said fluid, said piston means including first and second flexible membranes spaced from one another at opposed ends of said piston, said flexible members isolating a fluid containing chamber on one side of said piston from a variable volume chamber on the other side thereof so that said fluid does not pass around said piston into said variable volume chamber.

13. The pump assembly of claim 12 further comprising valve means for controlling the pressure in said variable volume chamber and between said flexible membranes to permit movement of said membranes with said piston as said piston reciprocates in said pump.

14. The pump assembly of claim 13 wherein said valve means for controlling said pressure comprises a first valve means connecting said variable volume chamber and the area between said flexible membranes, a second valve means for permitting air under pressure to egress from said variable volume chamber and a third valve means connected to first valve means and said area between said flexible membranes for controlling the air pressure in said variable volume chamber and said area between said flexible membranes.

15. The pump assembly of claim 20 wherein said program controls the volume of said fluid pumped with respect to time.

16. The pump assembly of claim 20 wherein said program controls the pressure of said fluid pumped with respect to time.

17. The pump assembly of claim 1 wherein said pump includes a hydraulic motor for driving said pump, and a servo valve for supplying hydraulic fluid to said hydraulic motor in accordance with said stored program.

18. The pump assembly of claim 6 wherein said controlling means comprises a digital-to-analog converter, said converter having its input connected to the output of said memory means and its output connected to said pump and to said clock generator.

* * * * *